United States Patent
Swift

(10) Patent No.: US 11,197,662 B2
(45) Date of Patent: *Dec. 14, 2021

(54) ILLUMINATED SURGICAL RETRACTOR

(71) Applicant: OBP SURGICAL CORPORATION, Lawrence, MA (US)

(72) Inventor: Jeffrey Ralph Swift, Boca Grande, FL (US)

(73) Assignee: OBP Surgical Corporation, Lawrence, MA (US)

( * ) Notice: Subject to any disclaimer, the term of this patent is extended or adjusted under 35 U.S.C. 154(b) by 138 days.

This patent is subject to a terminal disclaimer.

(21) Appl. No.: 16/536,727

(22) Filed: Aug. 9, 2019

(65) Prior Publication Data

US 2019/0357896 A1 Nov. 28, 2019

Related U.S. Application Data

(63) Continuation of application No. 15/846,957, filed on Dec. 19, 2017, now Pat. No. 10,420,540, which is a
(Continued)

(51) Int. Cl.
*A61B 17/02* (2006.01)
*A61B 90/30* (2016.01)
*A61B 17/00* (2006.01)

(52) U.S. Cl.
CPC .......... *A61B 17/0206* (2013.01); *A61B 17/02* (2013.01); *A61B 90/30* (2016.02);
(Continued)

(58) Field of Classification Search
CPC ..... A61B 17/02; A61B 17/0206; A61B 17/44; A61B 17/0218; A61B 17/42;
(Continued)

(56) References Cited

U.S. PATENT DOCUMENTS

| 559,122 A | 4/1896 | Daily |
| 659,182 A | 10/1900 | Pilling |

(Continued)

FOREIGN PATENT DOCUMENTS

| CN | 2239235 Y | 11/1996 |
| CN | 2265156 Y | 10/1997 |

(Continued)

OTHER PUBLICATIONS

The above documents were cited in a European Search Report dated Nov. 23, 2018, that issued in the corresponding European Patent Application No. 16747107.7.
(Continued)

*Primary Examiner* — Pedro Philogene
(74) *Attorney, Agent, or Firm* — Cowan, Liebowitz & Latman P.C.

(57) ABSTRACT

An illuminated surgical retractor comprising a blade having first and second opposing surfaces, a handle extending in a first direction at an angle from a proximal end of the blade, an illumination assembly comprising at least one direct light source positioned to directly emit light toward a distal end of the blade, wherein the first surface of the blade faces away from the first direction, the illumination assembly abuts the first surface of the blade, and the illumination assembly includes a cover partially enclosing the at least one light source and abutting the first surface of the blade.

21 Claims, 8 Drawing Sheets

Related U.S. Application Data continuation of application No. 14/614,413, filed on Feb. 5, 2015, now Pat. No. 9,867,602.

(52) U.S. Cl.
CPC ............... *A61B 2017/0023* (2013.01); *A61B 2017/00477* (2013.01); *A61B 2017/00734* (2013.01); *A61B 2090/309* (2016.02)

(58) Field of Classification Search
CPC ..... A61B 17/206; A61B 17/218; A61B 17/32; A61B 2017/0023; A61B 2017/00477; A61B 2017/00734; A61B 2090/309; A61B 90/30; A61B 1/32; A61B 1/0032; A61B 1/0066; A61B 1/015; A61B 1/0684; A61B 1/07; A61B 1/303; A61B 1/0669
USPC .................................................. 600/184-246
See application file for complete search history.

(56) References Cited

U.S. PATENT DOCUMENTS

| | | |
|---|---|---|
| 2,235,979 A | 3/1941 | Brown |
| 2,247,458 A | 6/1941 | Shepard |
| 2,482,971 A | 9/1949 | Golson |
| 2,592,190 A | 4/1952 | Rubens et al. |
| 3,324,850 A | 6/1967 | Gunning et al. |
| 3,332,414 A | 7/1967 | Gasper |
| 3,532,088 A | 10/1970 | Fiore |
| 3,592,199 A | 7/1971 | Ostensen |
| 3,595,222 A | 7/1971 | Vellacott |
| 3,638,644 A | 2/1972 | Reick |
| 3,675,641 A | 7/1972 | Fiore |
| 3,716,047 A | 2/1973 | Moore et al. |
| 3,729,006 A | 4/1973 | Wilder et al. |
| 3,762,400 A | 10/1973 | McDonald |
| 3,769,968 A | 11/1973 | Blount et al. |
| 3,789,835 A | 2/1974 | Whitman |
| 3,815,585 A | 6/1974 | Fiore |
| 3,826,248 A | 7/1974 | Gobels |
| 3,851,642 A | 12/1974 | McDonald |
| 3,934,578 A | 1/1976 | Heine |
| 3,945,371 A | 3/1976 | Adelman |
| 3,978,850 A | 9/1976 | Moore et al. |
| 4,067,323 A | 1/1978 | Troutner |
| 4,156,424 A | 5/1979 | Burgin |
| 4,210,133 A | 7/1980 | Castaneda |
| 4,226,228 A | 10/1980 | Shin et al. |
| 4,263,899 A | 4/1981 | Burgin |
| 4,300,541 A | 11/1981 | Burgin |
| 4,337,763 A | 7/1982 | Petrassevich |
| 4,432,351 A | 2/1984 | Hoary |
| 4,492,220 A | 1/1985 | Hayes |
| 4,502,468 A | 3/1985 | Burgin |
| 4,527,553 A | 7/1985 | Upsher |
| 4,546,761 A | 10/1985 | McCullough |
| 4,551,129 A | 11/1985 | Coleman et al. |
| 4,562,832 A | 1/1986 | Wilder |
| 4,566,439 A | 1/1986 | Burgin |
| 4,574,784 A | 3/1986 | Soloway |
| 4,597,383 A | 7/1986 | Van Der Bel |
| 4,607,623 A | 8/1986 | Bauman |
| 4,619,248 A | 10/1986 | Walsh |
| 4,638,792 A | 1/1987 | Burgin |
| 4,766,887 A | 8/1988 | Cecil, Jr. et al. |
| 4,807,600 A | 2/1989 | Hayes |
| 4,884,559 A | 12/1989 | Collins |
| 4,905,670 A | 3/1990 | Adair |
| 4,934,352 A | 6/1990 | Sullivan, Jr. |
| 4,971,036 A | 11/1990 | Collins |
| 5,018,507 A | 5/1991 | Montaldi |
| 5,026,368 A | 6/1991 | Adair |
| 5,054,906 A | 10/1991 | Lyons, Jr. |
| 5,063,908 A | 11/1991 | Collins |
| 5,143,054 A | 9/1992 | Adair |
| 5,165,387 A | 11/1992 | Woodson |
| 5,174,278 A | 12/1992 | Babkow |
| 5,179,937 A | 1/1993 | Lee |
| 5,179,938 A | 1/1993 | Lonky |
| 5,222,271 A | 6/1993 | Eganhouse |
| D337,384 S | 7/1993 | Schucman |
| 5,318,009 A | 6/1994 | Robinson |
| 5,329,938 A | 7/1994 | Lonky |
| 5,427,152 A | 6/1995 | Weber |
| 5,438,976 A | 8/1995 | Nash |
| 5,465,709 A | 11/1995 | Dickie et al. |
| 5,499,964 A | 3/1996 | Beck et al. |
| 5,512,038 A | 4/1996 | O'Neal et al. |
| 5,553,627 A | 9/1996 | Newkirk |
| 5,695,492 A | 12/1997 | Brown |
| 5,716,329 A | 2/1998 | Dieter |
| 5,785,648 A | 7/1998 | Min |
| 5,840,013 A | 11/1998 | Lee et al. |
| 5,846,249 A | 12/1998 | Thompson |
| 5,865,729 A | 2/1999 | Meehan |
| 5,873,820 A | 2/1999 | Norell |
| 5,879,304 A | 3/1999 | Schuchman et al. |
| 5,888,195 A | 3/1999 | Schneider |
| 5,899,854 A | 5/1999 | Slishman |
| 5,916,150 A | 6/1999 | Sillman |
| 5,967,971 A | 10/1999 | Bolser |
| 6,001,077 A | 12/1999 | Ellman et al. |
| 6,004,265 A | 12/1999 | Hsu et al. |
| 6,036,638 A | 3/2000 | Nwawka |
| 6,036,713 A | 3/2000 | Kieturakis |
| 6,048,308 A | 4/2000 | Strong |
| 6,080,105 A | 6/2000 | Spears |
| 6,130,520 A | 10/2000 | Wawro et al. |
| 6,176,824 B1 | 1/2001 | Davis |
| 6,186,944 B1 | 2/2001 | Tsai |
| 6,217,512 B1 | 4/2001 | Salo et al. |
| 6,231,505 B1 | 5/2001 | Martin |
| 6,231,506 B1 | 5/2001 | Hu et al. |
| 6,254,247 B1 | 7/2001 | Carson |
| 6,277,067 B1 | 8/2001 | Blair |
| 6,319,199 B1 | 11/2001 | Sheehan et al. |
| 6,346,085 B1 | 2/2002 | Schiffman |
| 6,359,644 B1 | 3/2002 | Salvati |
| 6,361,489 B1 | 3/2002 | Tsai |
| 6,363,763 B1 | 4/2002 | Geringer et al. |
| 6,379,296 B1 | 4/2002 | Baggett |
| 6,379,299 B1 | 4/2002 | Borodulin et al. |
| 6,394,111 B1 | 5/2002 | Jacobs et al. |
| 6,394,950 B1 | 5/2002 | Weiss |
| 6,413,208 B1 | 7/2002 | Schöllhorn et al. |
| 6,416,465 B2 | 7/2002 | Brau |
| 6,428,180 B1 | 8/2002 | Karram et al. |
| 6,432,045 B2 | 8/2002 | Lemperle et al. |
| 6,432,049 B1 | 8/2002 | Banta |
| 6,436,033 B2 | 8/2002 | Tan |
| 6,450,952 B1 | 9/2002 | Rioux |
| 6,468,206 B1 | 10/2002 | Hipps et al. |
| 6,468,232 B1 | 10/2002 | Ashton-Miller et al. |
| 6,487,440 B2 | 11/2002 | Deckert et al. |
| 6,504,985 B2 | 1/2003 | Parker et al. |
| 6,523,973 B2 | 2/2003 | Galli |
| 6,524,259 B2 | 2/2003 | Baxter-Jones et al. |
| 6,569,091 B2 | 5/2003 | Diokno et al. |
| 6,589,168 B2 | 7/2003 | Thompson |
| 6,595,917 B2 | 7/2003 | Nieto |
| 6,616,603 B1 | 9/2003 | Fontana |
| 6,626,825 B2 | 9/2003 | Tsai |
| 6,663,576 B2 | 12/2003 | Gombrich et al. |
| 6,676,598 B2 | 1/2004 | Rudischhauser et al. |
| 6,719,688 B2 | 4/2004 | Pecherer et al. |
| 6,761,687 B1 | 7/2004 | Doshi |
| 6,830,547 B2 | 12/2004 | Weiss |
| 6,896,653 B1 | 5/2005 | Vail, III et al. |
| 7,014,340 B2 | 3/2006 | Betis |
| 7,029,439 B2 | 4/2006 | Roberts et al. |
| D520,464 S | 5/2006 | Strong |
| 7,223,223 B2 | 5/2007 | Lindsay |

(56) References Cited

U.S. PATENT DOCUMENTS

| | | | |
|---|---|---|---|
| 7,276,025 B2 | 10/2007 | Roberts et al. | |
| 7,306,559 B2 | 12/2007 | Williams | |
| 7,492,116 B2 | 2/2009 | Oleynikov et al. | |
| 7,631,981 B2 | 12/2009 | Miller et al. | |
| 7,736,304 B2 | 6/2010 | Pecherer | |
| 7,758,203 B2 | 7/2010 | McMahon et al. | |
| 7,845,824 B2 | 12/2010 | Robotham | |
| 7,878,973 B2 | 2/2011 | Yee et al. | |
| 7,909,759 B2 | 3/2011 | Pecherer | |
| 7,967,809 B2 | 6/2011 | Jay-Robinson | |
| 8,012,089 B2 | 9/2011 | Bayat | |
| 8,047,987 B2 | 11/2011 | Grey et al. | |
| 8,052,702 B2 | 11/2011 | Hess et al. | |
| 8,088,066 B2 * | 1/2012 | Grey | A61B 17/02 600/212 |
| 8,096,945 B2 * | 1/2012 | Buchok | A61B 1/00137 600/205 |
| 8,142,352 B2 | 3/2012 | Vivenzio et al. | |
| 8,142,353 B2 | 3/2012 | Pecherer et al. | |
| 8,157,728 B2 | 4/2012 | Danna et al. | |
| 8,162,826 B2 | 4/2012 | Pecherer et al. | |
| 8,251,898 B2 | 8/2012 | Pecherer | |
| 8,292,805 B2 | 10/2012 | Vayser et al. | |
| 8,317,693 B2 | 11/2012 | Grey et al. | |
| 8,388,523 B2 | 3/2013 | Vivenzio et al. | |
| 8,394,017 B2 | 3/2013 | Kieffer | |
| 8,435,175 B2 | 5/2013 | McMahon et al. | |
| 8,512,234 B2 | 8/2013 | Grey et al. | |
| 8,512,237 B2 | 8/2013 | Bastia | |
| 8,555,892 B2 | 10/2013 | Traub | |
| 8,596,847 B2 | 12/2013 | Vayser et al. | |
| 8,628,879 B2 | 1/2014 | Pecherer et al. | |
| 8,651,704 B1 | 2/2014 | Gordin et al. | |
| 8,795,162 B2 | 8/2014 | Vayser et al. | |
| 8,821,385 B2 | 9/2014 | Naito | |
| 8,870,761 B2 | 10/2014 | Vayser et al. | |
| D719,652 S | 12/2014 | Swift | |
| 8,979,745 B2 | 3/2015 | Swift | |
| 9,002,159 B2 | 4/2015 | Sutherland et al. | |
| 9,044,161 B2 | 6/2015 | Vayser et al. | |
| 9,050,048 B2 | 6/2015 | Nadershahi | |
| 9,072,452 B2 | 7/2015 | Vayser et al. | |
| 9,173,648 B2 * | 11/2015 | Vayser | B22F 7/08 |
| D745,669 S | 12/2015 | Swift | |
| 9,241,617 B2 | 1/2016 | Grey et al. | |
| D752,217 S | 3/2016 | Swift | |
| 9,271,709 B2 | 3/2016 | Grey et al. | |
| 9,271,710 B2 | 3/2016 | Grey et al. | |
| 9,282,878 B2 | 3/2016 | Grey et al. | |
| D753,295 S | 4/2016 | Vivenzio et al. | |
| 9,307,897 B2 | 4/2016 | Swift | |
| 9,308,054 B2 | 4/2016 | Vayser et al. | |
| 9,332,898 B2 | 5/2016 | McMahon et al. | |
| 9,468,366 B2 | 10/2016 | Grey et al. | |
| 9,510,737 B2 | 12/2016 | Vayser et al. | |
| 9,532,706 B2 | 1/2017 | McMahon et al. | |
| 9,629,529 B1 | 4/2017 | Indovina et al. | |
| 9,636,182 B2 | 5/2017 | Vayser et al. | |
| 9,718,130 B1 | 8/2017 | Vayser et al. | |
| 9,763,743 B2 | 9/2017 | Lin et al. | |
| 9,808,231 B2 | 11/2017 | Miraki et al. | |
| 9,814,377 B2 | 11/2017 | Lia et al. | |
| 9,820,638 B2 | 11/2017 | Cheng | |
| 9,820,729 B2 | 11/2017 | Miles et al. | |
| 9,826,892 B2 | 11/2017 | Dresher et al. | |
| 9,833,295 B2 | 12/2017 | Vayser et al. | |
| 9,833,308 B2 | 12/2017 | Dye | |
| 9,844,364 B2 | 12/2017 | Grey et al. | |
| 9,861,349 B2 | 1/2018 | Nadershahi et al. | |
| 9,867,531 B2 | 1/2018 | Pacey et al. | |
| 9,867,602 B2 * | 1/2018 | Swift | A61B 17/02 |
| 9,877,639 B2 | 1/2018 | Grey et al. | |
| 9,877,644 B2 | 1/2018 | Greenstein et al. | |
| D809,660 S | 2/2018 | Nguyen et al. | |
| 9,883,792 B2 | 2/2018 | McMahon et al. | |
| 9,888,957 B2 | 2/2018 | Wolf et al. | |
| 9,907,544 B2 | 3/2018 | Nadershahi et al. | |
| 9,913,682 B2 | 3/2018 | Wolf et al. | |
| 9,918,618 B2 | 3/2018 | Molnar | |
| 9,918,802 B2 | 3/2018 | Coppersmith et al. | |
| 9,931,028 B2 | 4/2018 | Lia et al. | |
| 9,943,295 B2 | 4/2018 | King | |
| 9,949,814 B2 | 4/2018 | Alexander et al. | |
| 9,955,858 B2 | 5/2018 | Pamnani et al. | |
| 9,968,262 B2 | 5/2018 | Greenstein et al. | |
| 9,968,346 B2 | 5/2018 | Alexander et al. | |
| 9,980,710 B2 | 5/2018 | Seifert et al. | |
| 9,986,901 B2 | 6/2018 | Grey et al. | |
| 9,986,903 B2 | 6/2018 | Nadershahi et al. | |
| 9,986,988 B2 | 6/2018 | Ferro et al. | |
| 9,999,345 B2 | 6/2018 | Vayser et al. | |
| 10,004,392 B2 | 6/2018 | Millard et al. | |
| 10,004,393 B2 | 6/2018 | Kucklick | |
| 10,028,648 B2 | 7/2018 | Goldfain et al. | |
| 10,028,649 B2 | 7/2018 | Salvati et al. | |
| 10,028,780 B2 | 7/2018 | Wolf et al. | |
| 10,045,686 B2 | 8/2018 | Ou Yang et al. | |
| 10,045,731 B2 | 8/2018 | Prasad et al. | |
| 10,052,432 B2 | 8/2018 | Dexter et al. | |
| 10,064,611 B2 | 9/2018 | Ross et al. | |
| 10,064,613 B2 | 9/2018 | Davis et al. | |
| 10,068,173 B2 | 9/2018 | Vayser et al. | |
| 10,092,176 B2 | 10/2018 | Kienzle et al. | |
| 10,092,281 B2 | 10/2018 | Perler et al. | |
| 10,098,530 B2 | 10/2018 | McMahon et al. | |
| 10,105,043 B2 | 10/2018 | George | |
| 10,117,646 B2 | 11/2018 | Friedrich et al. | |
| 10,130,441 B2 | 11/2018 | Martinez | |
| 10,166,016 B2 | 1/2019 | Shimizu et al. | |
| 10,172,601 B2 | 1/2019 | Ahn | |
| 10,174,933 B2 | 1/2019 | Phillips, Jr. et al. | |
| 10,188,298 B2 | 1/2019 | Greenstein et al. | |
| 10,213,271 B2 | 2/2019 | Duggal et al. | |
| 10,219,800 B2 | 3/2019 | Tsubouchi | |
| 10,220,445 B2 | 3/2019 | Vayser et al. | |
| 10,226,555 B2 | 3/2019 | Vayser et al. | |
| 10,238,462 B2 | 3/2019 | Wood et al. | |
| D846,119 S | 4/2019 | Greeley et al. | |
| 10,278,571 B2 | 5/2019 | Poormand | |
| 10,292,782 B2 | 5/2019 | Haverich et al. | |
| 10,292,784 B2 | 5/2019 | Duggal et al. | |
| 10,342,525 B2 | 7/2019 | Wilson | |
| 10,420,540 B2 * | 9/2019 | Swift | A61B 17/0206 |
| 2001/0029044 A1 | 10/2001 | Gombrich et al. | |
| 2002/0022769 A1 | 2/2002 | Smith et al. | |
| 2002/0038075 A1 | 3/2002 | Tsai | |
| 2002/0038076 A1 | 3/2002 | Sheehan et al. | |
| 2002/0055670 A1 | 5/2002 | Weiss | |
| 2002/0115909 A1 | 8/2002 | Bolser | |
| 2002/0156350 A1 | 10/2002 | Nieto | |
| 2002/0165435 A1 | 11/2002 | Weiss | |
| 2002/0198471 A1 | 12/2002 | Baxter-Jones et al. | |
| 2003/0095781 A1 | 5/2003 | Willaims | |
| 2003/0105387 A1 | 6/2003 | Frumovitz et al. | |
| 2003/0139673 A1 | 7/2003 | Vivenzio et al. | |
| 2003/0158502 A1 | 8/2003 | Baxter-Jones et al. | |
| 2003/0176772 A1 | 9/2003 | Yang | |
| 2003/0187331 A1 | 10/2003 | Faludi et al. | |
| 2004/0026829 A1 | 2/2004 | Van Der Weegen | |
| 2004/0054260 A1 | 3/2004 | Klaassen et al. | |
| 2004/0141175 A1 | 7/2004 | Baldwin et al. | |
| 2004/0183482 A1 | 9/2004 | Roberts et al. | |
| 2004/0184288 A1 | 9/2004 | Bettis | |
| 2004/0186355 A1 | 9/2004 | Strong | |
| 2004/0254428 A1 | 12/2004 | Ritland | |
| 2005/0065496 A1 | 3/2005 | Simon et al. | |
| 2005/0085699 A1 | 4/2005 | Weiss | |
| 2005/0085723 A1 | 4/2005 | Huebner | |
| 2005/0093718 A1 | 5/2005 | Martin | |
| 2005/0125015 A1 | 6/2005 | McNally-Heintzelman et al. | |
| 2005/0159649 A1 | 7/2005 | Patel | |
| 2005/0182301 A1 | 8/2005 | Acker et al. | |
| 2005/0192482 A1 | 9/2005 | Carpenter | |
| 2005/0215858 A1 | 9/2005 | Vail, III | |

(56) References Cited

U.S. PATENT DOCUMENTS

| | | |
|---|---|---|
| 2005/0240081 A1 | 10/2005 | Eliachar |
| 2005/0277811 A1 | 12/2005 | Richards et al. |
| 2006/0084843 A1 | 4/2006 | Sommerich et al. |
| 2006/0155276 A1 | 7/2006 | Walulik et al. |
| 2006/0189847 A1 | 8/2006 | Yee et al. |
| 2006/0200186 A1 | 9/2006 | Marchek et al. |
| 2007/0043264 A1 | 2/2007 | Gillis et al. |
| 2007/0060795 A1 | 3/2007 | Vayser et al. |
| 2007/0060938 A1 | 3/2007 | Dziadik et al. |
| 2007/0066872 A1 | 3/2007 | Morrison et al. |
| 2007/0100212 A1 | 5/2007 | Pimenta et al. |
| 2007/0208226 A1 | 9/2007 | Grey et al. |
| 2007/0230164 A1 | 10/2007 | Vivenzio et al. |
| 2007/0230167 A1 | 10/2007 | McMahon et al. |
| 2007/0255110 A1 | 11/2007 | Wax et al. |
| 2007/0270866 A1 | 11/2007 | Von Jako |
| 2007/0287888 A1 | 12/2007 | Lovell et al. |
| 2008/0002426 A1 | 1/2008 | Vayser et al. |
| 2008/0027461 A1 | 1/2008 | Vaquero et al. |
| 2008/0113312 A1 | 5/2008 | Ortega |
| 2008/0221569 A1 | 9/2008 | Moore et al. |
| 2008/0228038 A1 | 9/2008 | McMahon et al. |
| 2008/0269564 A1 | 10/2008 | Gelnett |
| 2008/0269565 A1 | 10/2008 | McMahon et al. |
| 2008/0278936 A1 | 11/2008 | Kurth et al. |
| 2009/0018400 A1 | 1/2009 | Raymond et al. |
| 2009/0069634 A1 | 3/2009 | Larkin |
| 2009/0097236 A1 | 4/2009 | Miller et al. |
| 2009/0112068 A1 | 4/2009 | Grey et al. |
| 2009/0275803 A1 | 11/2009 | Krauter et al. |
| 2009/0287192 A1 | 11/2009 | Vivenzio et al. |
| 2009/0312610 A1 | 12/2009 | Buchok et al. |
| 2010/0036382 A1 | 2/2010 | Bonnadier |
| 2010/0041955 A1 | 2/2010 | Grey et al. |
| 2010/0097794 A1 | 4/2010 | Teng et al. |
| 2010/0190129 A1 | 7/2010 | Paz |
| 2010/0191062 A1 | 7/2010 | Kieffer |
| 2010/0292533 A1 | 11/2010 | Kasahara et al. |
| 2011/0275894 A1 | 11/2011 | Mackin |
| 2012/0055470 A1 | 3/2012 | Pecherer et al. |
| 2012/0059226 A1 | 3/2012 | Funt |
| 2012/0078060 A1 | 3/2012 | Swift |
| 2012/0116170 A1 | 5/2012 | Vayser et al. |
| 2012/0232352 A1 | 9/2012 | Lin et al. |
| 2012/0243212 A1 | 9/2012 | Smith et al. |
| 2013/0018230 A1 | 1/2013 | Su et al. |
| 2013/0021798 A1 | 1/2013 | Chen et al. |
| 2013/0041229 A2 | 2/2013 | Hahn et al. |
| 2013/0102850 A1 | 4/2013 | Fiorella |
| 2013/0102887 A1 | 4/2013 | Thompson et al. |
| 2013/0109910 A1 | 5/2013 | Alexander et al. |
| 2013/0158345 A1 | 6/2013 | Majlessi |
| 2013/0197313 A1 | 8/2013 | Wan |
| 2013/0245657 A1 | 9/2013 | Deville et al. |
| 2013/0267786 A1 | 10/2013 | Vayser et al. |
| 2013/0281784 A1 | 10/2013 | Ray |
| 2013/0324801 A1 | 12/2013 | Grey et al. |
| 2014/0088371 A1 | 3/2014 | Vayser et al. |
| 2014/0179998 A1 | 6/2014 | Pacey |
| 2014/0202459 A1 | 7/2014 | Iqbal |
| 2014/0228875 A1 | 8/2014 | Saadat |
| 2014/0257039 A1 | 9/2014 | Feldman |
| 2014/0275790 A1 | 9/2014 | Vivenzio et al. |
| 2014/0309499 A1 | 10/2014 | Swift |
| 2014/0316211 A1 | 10/2014 | Hermle |
| 2014/0323800 A1 | 10/2014 | Dye |
| 2014/0323811 A1 | 10/2014 | DeSantis et al. |
| 2014/0364695 A1 | 12/2014 | Nadershahi et al. |
| 2014/0371536 A1* | 12/2014 | Miller ............... B29C 45/1676 600/195 |
| 2015/0018625 A1 | 1/2015 | Miraki et al. |
| 2015/0157469 A1 | 6/2015 | Prado et al. |
| 2015/0238070 A1 | 8/2015 | Lia et al. |
| 2015/0285382 A1 | 10/2015 | Kienreich et al. |
| 2015/0297217 A1 | 10/2015 | Huitema et al. |
| 2016/0000305 A1 | 1/2016 | Elbaz et al. |
| 2016/0030128 A1 | 2/2016 | Duggal et al. |
| 2016/0038032 A1 | 2/2016 | Dan |
| 2016/0066915 A1 | 3/2016 | Baber et al. |
| 2016/0081833 A1 | 3/2016 | Leblanc et al. |
| 2016/0095506 A1 | 4/2016 | Dan et al. |
| 2016/0100751 A1 | 4/2016 | Davis et al. |
| 2016/0151058 A1 | 6/2016 | Ferro et al. |
| 2016/0302657 A1 | 10/2016 | Hussey et al. |
| 2017/0007228 A1 | 1/2017 | Costabile |
| 2017/0020621 A1 | 1/2017 | Huldin et al. |
| 2017/0059400 A1 | 3/2017 | Murphy et al. |
| 2017/0065282 A1 | 3/2017 | Mathis et al. |
| 2017/0079518 A1 | 3/2017 | Elbaz et al. |
| 2017/0172404 A1 | 6/2017 | McMahon et al. |
| 2017/0172555 A1 | 6/2017 | Shimizu et al. |
| 2017/0181605 A1 | 6/2017 | Lalli et al. |
| 2017/0181607 A1 | 6/2017 | Lalli et al. |
| 2017/0181615 A1 | 6/2017 | Vella et al. |
| 2017/0181616 A1 | 6/2017 | Vella et al. |
| 2017/0224206 A1 | 8/2017 | Vayser |
| 2017/0231712 A1 | 8/2017 | Vayser |
| 2017/0296162 A1 | 10/2017 | Wan |
| 2017/0300623 A1 | 10/2017 | Rosenblatt et al. |
| 2017/0303903 A1 | 10/2017 | De Koning et al. |
| 2017/0347871 A1 | 12/2017 | Wallace et al. |
| 2017/0360423 A1 | 12/2017 | Stevenson et al. |
| 2018/0000469 A1 | 1/2018 | Wood et al. |
| 2018/0008137 A1 | 1/2018 | Poormand |
| 2018/0008138 A1 | 1/2018 | Thommen et al. |
| 2018/0008368 A1 | 1/2018 | Duggal et al. |
| 2018/0014721 A1 | 1/2018 | Rullo et al. |
| 2018/0014842 A1 | 1/2018 | Shener-Irmakoglu |
| 2018/0014900 A1 | 1/2018 | Vayser et al. |
| 2018/0036095 A1 | 2/2018 | Vayser et al. |
| 2018/0042596 A1 | 2/2018 | Tsubouchi |
| 2018/0064316 A1 | 3/2018 | Charles et al. |
| 2018/0064317 A1 | 3/2018 | Tesar |
| 2018/0078301 A1 | 3/2018 | Vayser |
| 2018/0116581 A1 | 5/2018 | Prasad et al. |
| 2018/0125336 A1 | 5/2018 | Goldfarb et al. |
| 2018/0125347 A1 | 5/2018 | Czyzewski et al. |
| 2018/0132710 A1 | 5/2018 | Pacey et al. |
| 2018/0132970 A1 | 5/2018 | Ritter |
| 2018/0153391 A1 | 6/2018 | McMahon et al. |
| 2018/0156448 A1 | 6/2018 | Phillips, Jr. et al. |
| 2018/0206832 A1 | 7/2018 | Greeley et al. |
| 2018/0228376 A1 | 8/2018 | Greenstein et al. |
| 2018/0228483 A1 | 8/2018 | Duggal et al. |
| 2018/0235444 A1 | 8/2018 | Tsai |
| 2018/0235592 A1 | 8/2018 | Kass et al. |
| 2018/0249902 A1 | 9/2018 | Grey et al. |
| 2018/0263480 A1 | 9/2018 | Lalli et al. |
| 2018/0271581 A1 | 9/2018 | Ou Yang et al. |
| 2018/0280011 A1 | 10/2018 | Ferro et al. |
| 2018/0296082 A1 | 10/2018 | Salvati et al. |
| 2018/0317746 A1 | 11/2018 | Lalli et al. |
| 2018/0317752 A1 | 11/2018 | Cybulski et al. |
| 2018/0317902 A1 | 11/2018 | Green et al. |
| 2018/0328572 A1 | 11/2018 | Kennedy et al. |
| 2019/0038273 A1 | 2/2019 | Perler et al. |
| 2019/0049655 A1 | 2/2019 | Zagatsky et al. |
| 2019/0076138 A1 | 3/2019 | Opperman |
| 2019/0083079 A1 | 3/2019 | Shimizu et al. |
| 2019/0133432 A1 | 5/2019 | Tsai |
| 2019/0143006 A1 | 5/2019 | Vayser et al. |
| 2019/0143414 A1 | 5/2019 | Vayser et al. |
| 2019/0150422 A1 | 5/2019 | Welch |
| 2019/0150725 A1 | 5/2019 | Ramanujam et al. |
| 2019/0150739 A1 | 5/2019 | Wawro et al. |
| 2019/0150786 A1 | 5/2019 | Vassallo et al. |
| 2019/0167111 A1 | 6/2019 | Greenstein et al. |
| 2019/0167378 A1 | 6/2019 | Wood et al. |
| 2019/0190293 A1 | 6/2019 | Wawro et al. |
| 2019/0223708 A1 | 7/2019 | Recanati et al. |
| 2019/0254512 A1 | 8/2019 | Spiertz |
| 2019/0335988 A1 | 11/2019 | Lia et al. |
| 2019/0343379 A1 | 11/2019 | Altamura |
| 2019/0365217 A1 | 12/2019 | Hegenberger |

(56) References Cited

U.S. PATENT DOCUMENTS

| | | |
|---|---|---|
| 2020/0008694 A1 | 1/2020 | Karla et al. |
| 2020/0046216 A1 | 2/2020 | Moein |
| 2020/0069171 A1 | 3/2020 | Miller et al. |
| 2020/0107714 A1 | 4/2020 | Bar-Or et al. |
| 2020/0253467 A1 | 8/2020 | Lees, Jr. et al. |
| 2020/0337541 A1 | 10/2020 | Vivenzio et al. |
| 2021/0145270 A1 | 5/2021 | Altamura |

FOREIGN PATENT DOCUMENTS

| | | |
|---|---|---|
| CN | 2516109 Y | 10/2002 |
| CN | 2629738 Y | 8/2004 |
| CN | 1565664 A | 1/2005 |
| CN | 2668152 Y | 1/2005 |
| CN | 1717195 A | 1/2006 |
| CN | 101179982 A | 5/2008 |
| CN | 201055387 Y | 5/2008 |
| CN | 203591245 U | 5/2008 |
| CN | 201139589 Y | 10/2008 |
| CN | 102415869 A | 4/2012 |
| CN | 103154793 A | 6/2013 |
| CN | 302536685 S | 8/2013 |
| CN | 103925266 A | 7/2014 |
| CN | 203898367 U | 10/2014 |
| CN | 102573700 B | 12/2014 |
| DE | 2128855 A | 12/1972 |
| DE | 10216618 A1 | 1/2003 |
| DE | 202004002963 U1 | 5/2004 |
| DE | 202005019780 U1 | 5/2006 |
| DE | 600 33 612 T2 | 12/2007 |
| DE | 202010017638 U | 5/2012 |
| EP | 0190014 A2 | 8/1986 |
| EP | 1074224 A2 | 7/2001 |
| FR | 2490478 A1 | 3/1982 |
| GB | 2505463 A | 5/2014 |
| RU | 2187972 C2 | 8/2002 |
| RU | 2308873 C2 | 10/2007 |
| WO | 9825512 A1 | 6/1998 |
| WO | 0137739 A1 | 5/2001 |
| WO | 01/62137 A2 | 8/2001 |
| WO | 03082123 A2 | 10/2003 |
| WO | 2004064624 A1 | 8/2004 |
| WO | 2006107877 A2 | 10/2006 |
| WO | 2006107878 A2 | 10/2006 |
| WO | 2007/084641 A2 | 7/2007 |
| WO | 2009/090383 A2 | 7/2009 |
| WO | 2009137017 A2 | 11/2009 |
| WO | 2013-044151 A1 | 3/2013 |
| WO | 2014-041172 A1 | 3/2014 |
| WO | 2015/164881 A1 | 10/2015 |
| WO | 2006121530 A2 | 11/2016 |
| WO | 2016196788 A1 | 12/2016 |

OTHER PUBLICATIONS

The above patent was cited in a Oct. 29, 2018 Chinese Office Action, that issued in Chinese Patent Application No. 201711159829.6.

International Search Report of PCT/US2018/054925, dated Oct. 9, 2018.

Pankaj Saxena, et al., Hydrodissection Technique of Harvesting Left Internal Thoracic Artery, Department of Cardiac Surgery, The Prince Charles Hospital, Chermside, Brisbane, Queensland, Australia, Thoracic Artery, Ann Thorac Surg., 2005; 80:335-6.

The above U.S. Publications documents #1 and #2 were cited in a Supplementary European Search Report dated Apr. 24, 2019, that issued in European Patent Application No. 16804432.9.

OBP Medical—OfficeSPEC, Premier Speculum for In-Office Procedures published Nov. 30, 2009 (1 page).

OBP Medical—ER-SPEC OBGYN Brochure published Nov. 19, 2014 (2 pages).

OBP Medical—ER-SPEC Brochure, Light Source Now 10X Brighter published Oct. 30, 2012 (1 page).

OBP Medical—ER-SPEC Product Presentation published Apr. 16, 2014 (12 pages).

OBP Medical—ER-SPEC Brochure published Apr. 11, 2013 (2 pages).

OBP Medical—ER-SPEC Brochure published Feb. 4, 2013 (2 pages).

OBP Medical—ER-SPEC Brochure, Light Source Now 10X Brighter published Jan. 23, 2013 (1 page).

Redefining illumination, Eikon LT Adapt SE For optimal precision and protection (2019), Stryker, www.stryker.com/surgical (3 pages).

International Search Report for International application No. PCT/US2016/016154 dated May 19, 2016 for corresponding U.S. application, U.S. Appl. No. 14/614,413.

International Search Report, for International application No. PCT/US2016/035508 dated Sep. 15, 2016 for corresponding U.S. application, U.S. Appl. No. 15/171,581.

International Search Report for International application No. PCT/US2016/036833 dated Jan. 19, 2017.

U S. Patent references 121-125 and U.S. Published Patent Application references 48 and 50 were cited in an Office Action issued in U.S. Appl. No. 15/171,581.

U S. Published Patent Application references 47, 49 and 51 were cited in a PCT Search Report issued in PCT Application No. PCT/US2017/042617.

The above foreign patent documents 18, 21, 22, 23 and 24 were cited in a Nov. 1, 2017 Chinese Office Action, that issued in Chinese Patent Application No. 201510543086.7.

The above foreign patent documents 21, 22 and 26 was cited in the Jul. 16, 2018 Chinese Office Action, that issued in Chinese Patent Application No. 201510543086.7.

Solvey, Techinical Data Sheet, lxef 1022 polyarylamide, Feb. 13, 2015, pp. 1-5.

http://www.makeitfrom.com/material-properties/Polyetheretheketone-PEEK, printed on Oct. 9, 2016, pp. 1-9.

International Search Report for International application No. PCT/US2021/017768 dated May 27, 2021.

International Search Report for International application No. PCT/US2021/014076 dated Apr. 15, 2021.

Supplementary European Search Report dated Oct. 6, 2021 issued in European Application No. 19757432.0.

* cited by examiner

ILLUMINATED SURGICAL RETRACTOR

CROSS-REFERENCE TO RELATED APPLICATIONS

This application is a continuation application of application Ser. No. 15/846,957 filed Dec. 19, 2017, which is a continuation application of application Ser. No. 14/614,413 filed Feb. 5, 2015, both applications entitled "ILLUMINATED SURGICAL RETRACTOR", the entire disclosures of which are incorporated herein by reference.

BACKGROUND

Technical Field

The present disclosure relates to illuminated surgical retractors.

Description of Related Art

Existing technology for illumination during surgical/medical procedures includes overhead illumination. This illumination comes from either overhead lighting or head mounted fiber optic systems. Traditional overhead lighting systems face numerous limitations. A direct exposure of the field from the overhead source is required. Changes in patient or surgeon positioning may interfere with the light source. Frequent adjustments provide an inconvenience for the surgeon and disrupt the surgical flow. Overhead lighting is frequently inadequate for surgery in deeper cavities where more intense focused illumination may be required. In addition, the alignment of the surgeon's head frequently interferes with the remote illumination and prevents light from reaching the field. Head mounted fiber optic systems are used frequently for more limited surgical exposures. However, these devices have numerous limitations. First, the surgeon is tethered by the light cord attached to the headset, limiting the mobility in the operating room. Second, the devices are associated with head and neck fatigue with frequent or prolonged use. Third, the devices require the surgeon to maintain a steady head and neck position to provide a constant and steady illumination of the field, fourth, the use of remote light sources and fiber bundles introduces tremendous inefficiencies into the system. A typical ten-foot long cable will lose by approximately 10% per foot of cable for a 300-watt light source, which results in much lower illumination than desired.

Other existing technology for illumination during surgical/medical procedures includes lighted surgical retractors. These retractors include integral or attached light sources which project light locally down the retractor blade. Existing lighted surgical retractors overcome the problems with overhead illumination but still suffer from several shortcomings. These retractors can generally be classified into two categories. The first category includes those with detachable light sources. This category allows the retractor to be re-used and therefore the retractor must be sterilized prior to re-use. Characteristics of most light sources are not compatible with many sterilization procedures. For example, it is uncommon for batteries to carry out high temperature sterilization. It is also difficult to completely remove organic material from light source assemblies. To overcome these difficulties, lighted surgical retractors with detachable light sources were created. These light sources are releasably attached to the retractor via tape or other adhesive or clip on mechanism. This class of lighted surgical retractors requires assembly prior to use and disassembly, cleaning, and sterilization after use. Such assembly, disassembly, cleaning, and sterilization represent significant time, cost, and inefficiency for the user.

The second category of lighted surgical retractors was created that consists of surgical retractors with light sources that are integrated into the retractor and are not removable. These lighted surgical retractors contain a power source in the retractor handle, an illumination device built into, or permanently attached to the blade, and some form of optical or electrical coupling between the power source and the illumination device. The power source can be batteries or a device that will plug into the wall. It could also be an optical power source that generates optical energy instead of electrical energy. The illumination device is either one or more LEDs, a fiber optic cable or an optical waveguide. The form of coupling is either wiring for an electrical connection, or a fiber optic cable or optical waveguide for optical coupling. This second category of lighted surgical retractors eliminates the problem of assembly and disassembly that the first category of surgical retractors suffers from. This second class of retractors still suffers from difficulty in cleaning and sterilization. Also, the techniques involved in integrating light source components into the handle and blade are generally costly. Recent evidence is emerging that procedures for cleaning and sterilization are often flawed in practice, resulting in possible cross contamination of patients. These deficiencies have prevented a widespread adoption of this second category of lighted surgical retractors.

The present disclosure will describe a new class of lighted surgical retractors that does not suffer from these known deficiencies. The present disclosure completely eliminates the risk of cross contamination by insuring that each retractor can be only used once. The present disclosure eliminates the costly electrical or optical interconnect systems required of previous disclosures. The present disclosure eliminates the requirement of assembly, disassembly, cleaning, and re-sterilization by the end user.

SUMMARY

A technical aspect of the present disclosure provides an illuminated surgical retractor, which can be discarded after a single use due to its intrinsic low cost.

According to an embodiment of the present disclosure, an illuminated surgical retractor includes a blade, a handle, a curved section and an illumination assembly. The blade has a top surface and a bottom surface. The handle extends at an angle from a proximal end of the blade. The curved section connects the handle to the blade. The illumination assembly includes at least one light source, at least one battery and an activation device for energizing the light source. The illumination assembly is attachable to the curved section.

In one or more embodiments of the present disclosure, the blade, the handle and the curved section are integrally molded.

In one or more embodiments of the present disclosure, a chemical capacity of the battery is sufficient for a single use.

In one or more embodiments of the present disclosure, the illumination assembly includes a light ease integrally molded.

In one or more embodiments of the present disclosure, the illumination assembly includes a plurality of retaining tabs protruded from the light case. The illuminated surgical retractor further includes a plurality of acceptance slots and an acceptance cavity. The acceptance slots are located vertically, horizontally or at an angle with the curved section, and are configured for accepting the retaining tabs. The acceptance cavity is in communication with the acceptance slots. When the retaining tabs ore inserted fully into the acceptance slots, the retaining tabs arrive at the acceptance cavity.

When compared with the prior art, the embodiments of the present disclosure mentioned above have at least the following advantages:

(1) The non-directional shape of the retaining tab allows the illumination assembly to be utilized with either vertically released molds or horizontally released molds. This use of a common illumination assembly for a wide variety of retractor shapes dramatically lowers the cost of the illuminated surgical retractor.

(2) The chemical capacity of the batteries is sufficient for only a single use and the illuminated surgical retractor is discarded after the single use. The intrinsic low cost of the present disclosure makes the illuminated surgical retractor economically attractive, and eliminates the inefficiency and expense of cleaning and re-sterilization.

BRIEF DESCRIPTION OF THE DRAWINGS

The disclosure can be more fully understood by reading the following detailed description of the embodiments, with reference made to the accompanying drawings as follows.

DETAILED DESCRIPTION

Figure 1:
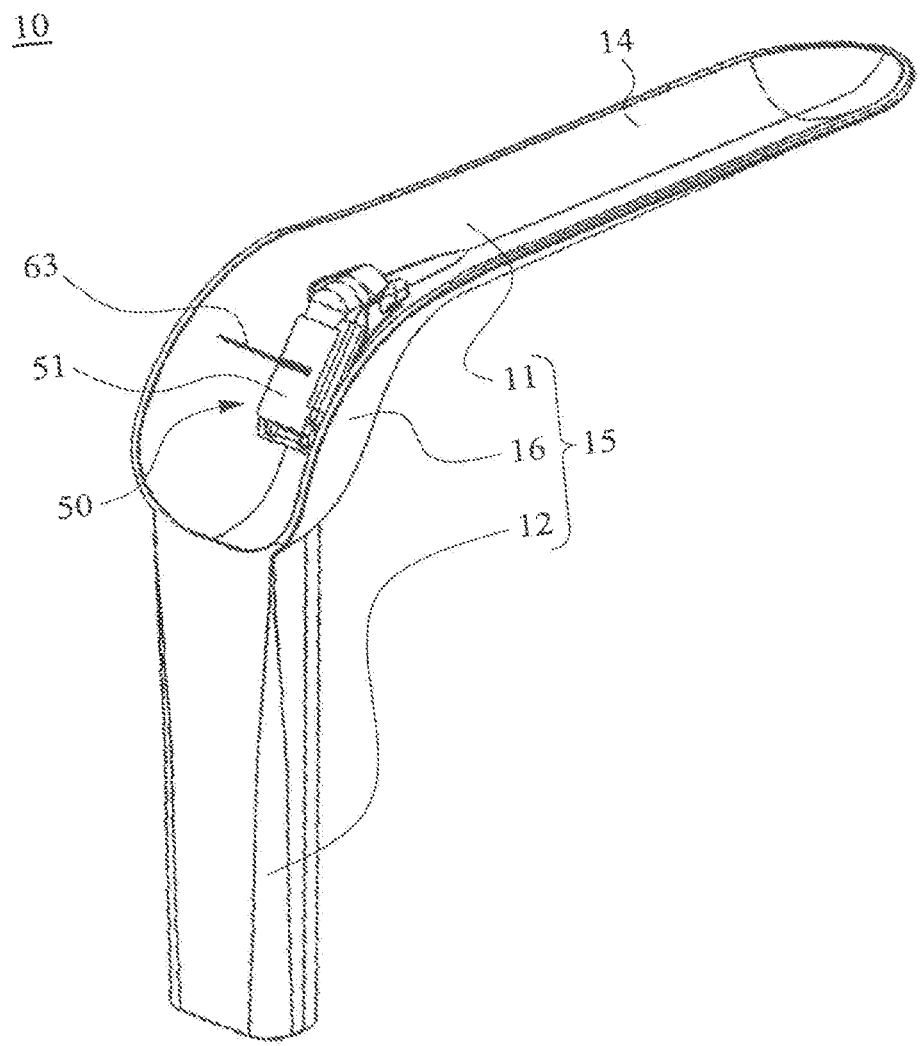
FIG. 1 is a schematic view of an illuminated surgical retractor according to an embodiment of the present disclosure.

Drawings will be used below to disclose a plurality of embodiments of the present disclosure. For the sake of clear illustration, many practical details will be explained together in the description below. However, it is appreciated that the practical details should not be used to limit the claimed scope. In other words, in some embodiments of the present disclosure, the practical details are not essential. Moreover, for the sake of drawing simplification, some customary structures and elements in the drawings will be schematically shown in a simplified way. Wherever possible, the same reference numbers are used in the drawings and the description to refer to the same or like parts.

Unless otherwise defined, all terms (including technical and scientific terms) used herein have the same meaning as commonly understood by one of ordinary skill in the art to which this disclosure belongs, it will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Figure 2:
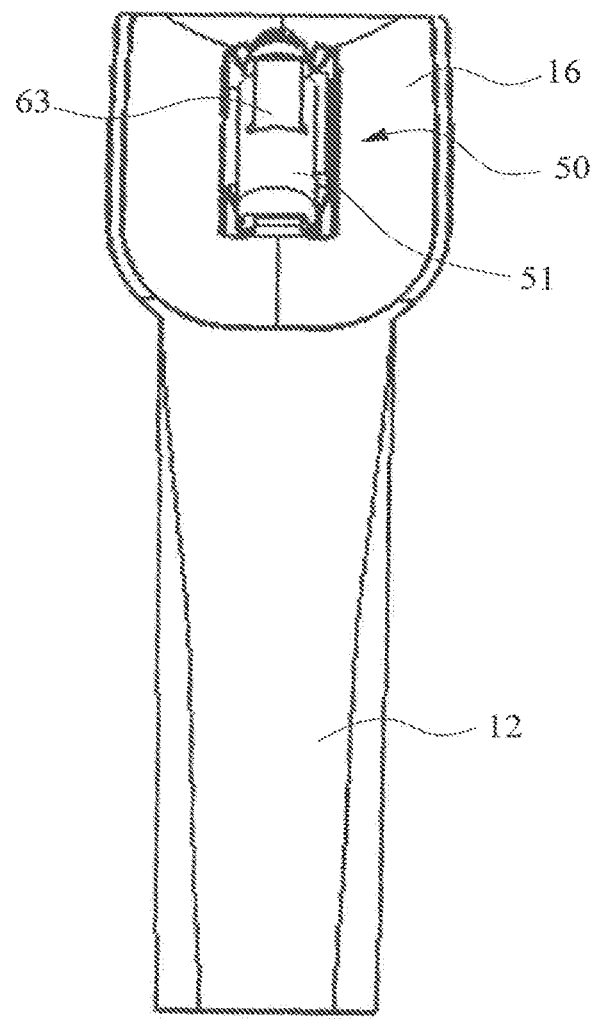
FIG. 2 is a rear view of the illuminated surgical retractor of FIG. 1.

Please refer to FIGS. 1-2. FIG. 1 is a schematic view of an illuminated surgical retractor 10 according to an embodiment of the present disclosure. FIG. 2 is a rear view of the illuminated surgical retractor 10 of FIG. 1. As shown in FIGS. 1-2, an illuminated surgical retractor 10 includes a blade 11, a handle 12, a curved section 16 and an illumination assembly 50. The blade 11 has a top surface 14 and a bottom surface. The handle 12 extends at an angle from a proximal end of the blade 11. The curved section 16 connects the handle 12 to the blade 11. The illumination assembly 50 includes at least one light source 64, at least one battery 62 and an activation device for energizing the light source 64. The illumination assembly 50 is attachable to the curved section 16.

Furthermore, the blade 11 and the handle 12 are joined together at an angle through the curved section 16 to form a retractor component 15. In practical applications, the blade 11, the handle 12 and the curved section 16 are integrally molded as a single piece. In addition, in this embodiment, the angle may be in a range of, for instance, 35 to 170 degrees, and can particularly be 90 degrees. The retractor component 15 may be made of any material, but preferably high strength plastic such as ABS or polyacrylamide and made by a low cost manufacturing process such as injection molding. The top surface 14 of the blade 11 may be concave (or flat, or convex). The blade 11 may have uniform width or may be shaped such that the distal end is wider or narrower than the proximal end. The blade 11 may have a lip at the end of it for retaining tissue, or may be curved as shown to prevent retention of tissue. In this embodiment, the handle 12 is in a rectangular form, but in other embodiments, the handle 12 may be circular or oval in shape, and may be opened on one or more sides. The illumination assembly 50 is integrated into she angular space connecting the blade 11 with the handle 12. Integration into this angular space allow the batteries 62 and the illumination assembly 50 to reside in a light enclosure 51 and eliminates the electrical or optical coupling requirements in previous disclosures.

Figure 3:
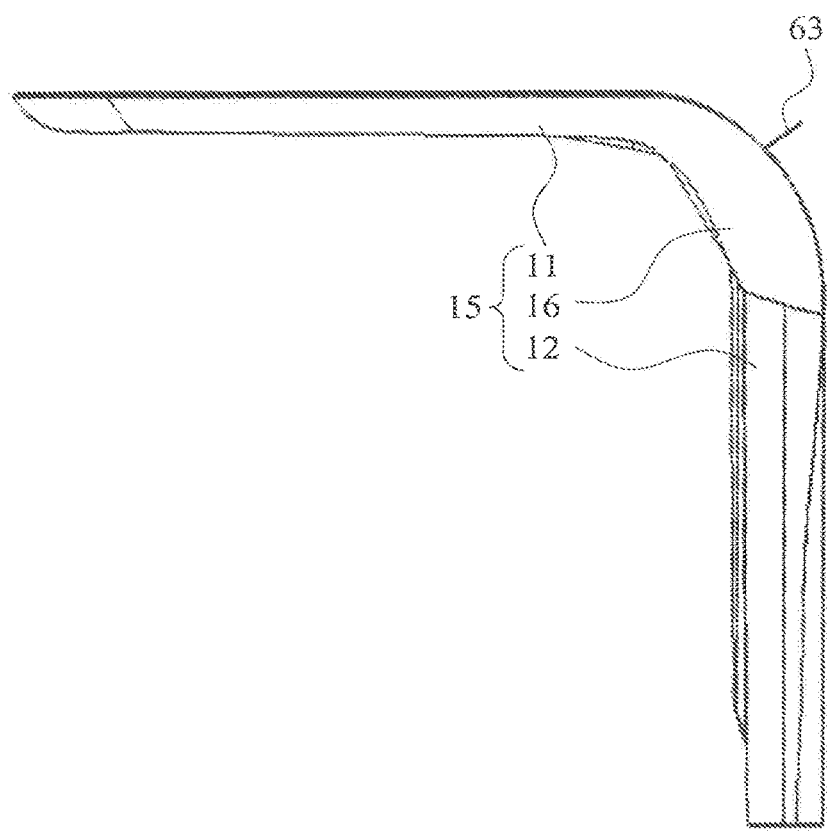
FIG. 3 is a side view of the illuminated surgical retractor of FIG. 1.

Please refer to FIG. 3. FIG. 3 is a side view of the illuminated surgical retractor 10 of FIG. 1. In this embodiment, as shown in FIG. 3, the removal of pull tab 63 is used to energize the illumination assembly 50. Other embodiments of the present disclosure may include the use of an electrical switch.

Figure 4:
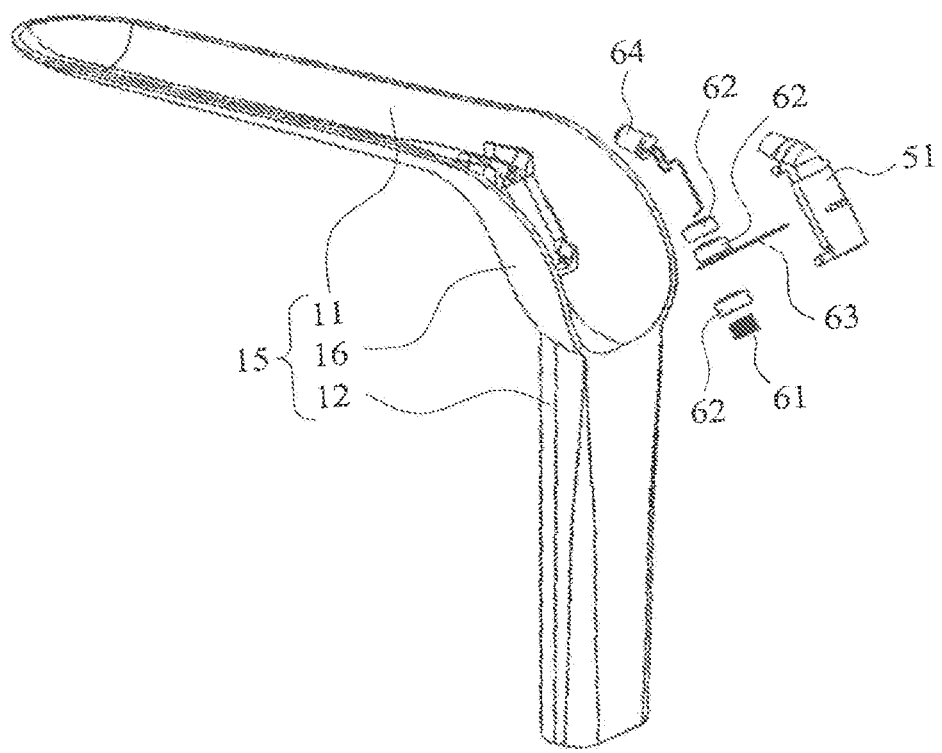
FIG. 4 is an exploded view of the illuminated surgical retractor of FIG. 1.

Please refer to FIG. 4. FIG. 4 is an exploded view of the illuminated surgical retractor 10 of FIG. 1. The light source 64 is used to provide illumination to the area of the blade 11 of the illuminated surgical retractor 10. The light source 64 can be a light emitting diode (LED), an incandescent element or a fluorescent element. However, this does not intend to limit the present disclosure. In this embodiment, the light source 64 is angled so that substantially all of the light travels to the distal end of the blade 11. In other embodiments, the light source 64 can be angled so as to provide substantially all of the light above the blade 11, or at other angles to the blade 11 that are preferable for the medical application of the illuminated surgical retractor 10. The batteries 62 provide power to the light source 64. The batteries 62 are small enough to be contained in the angled space between the blade 11 and the handle 12. Examples of the batteries 62 include LR41 or AG3 type button batteries. These batteries 62 are of a very low price. In the present embodiment, three batteries 62 are used to provide power to the light source 64. Three batteries 62 eliminate the need for expensive circuitry to condition the voltage and current required by the light source 64. These batteries 62 contain sufficient energy for 20-40 minutes of use, which is sufficient for the vast majority of medical procedures. In other embodiments, a different number and type of batteries 62 can be used with or without conditioning circuitry.

Figure 5:
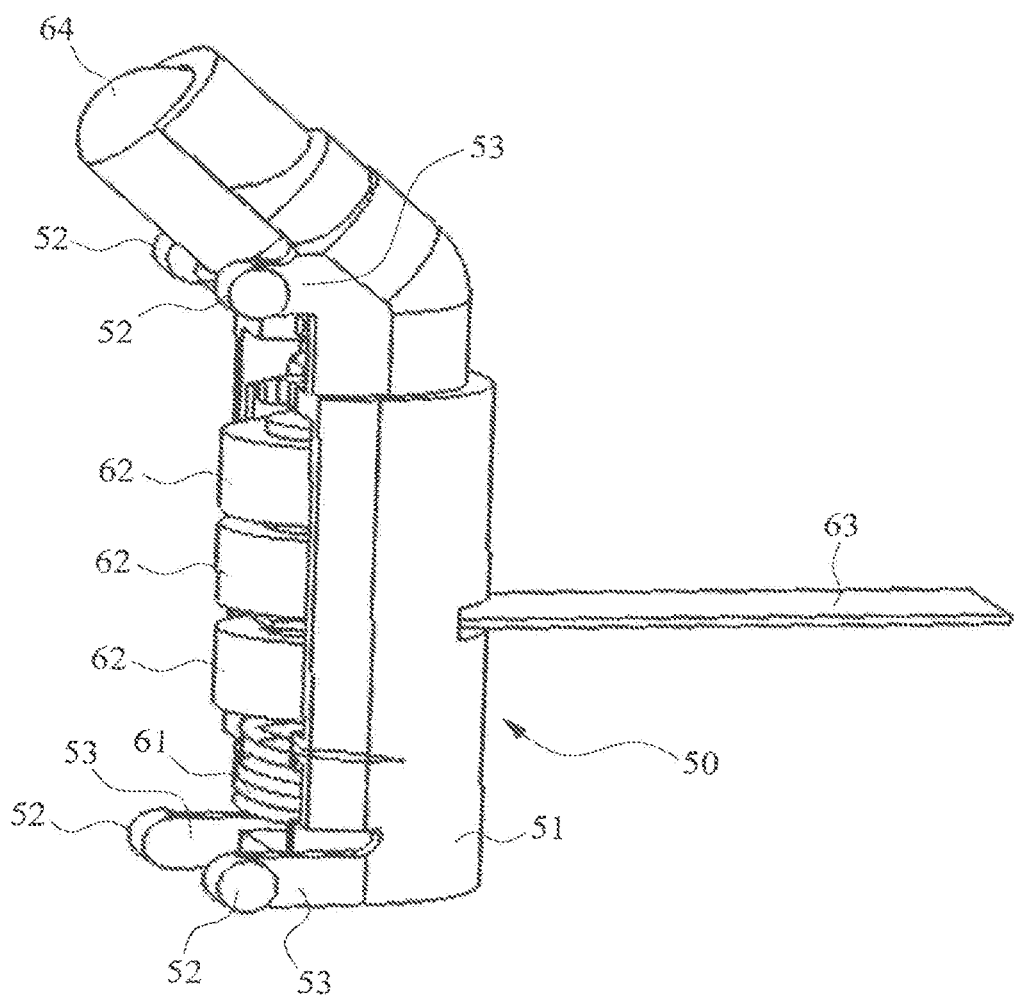
FIG. 5 is a schematic view of the illumination assembly of the illuminated surgical retractor of FIG. 1.
Figure 6:
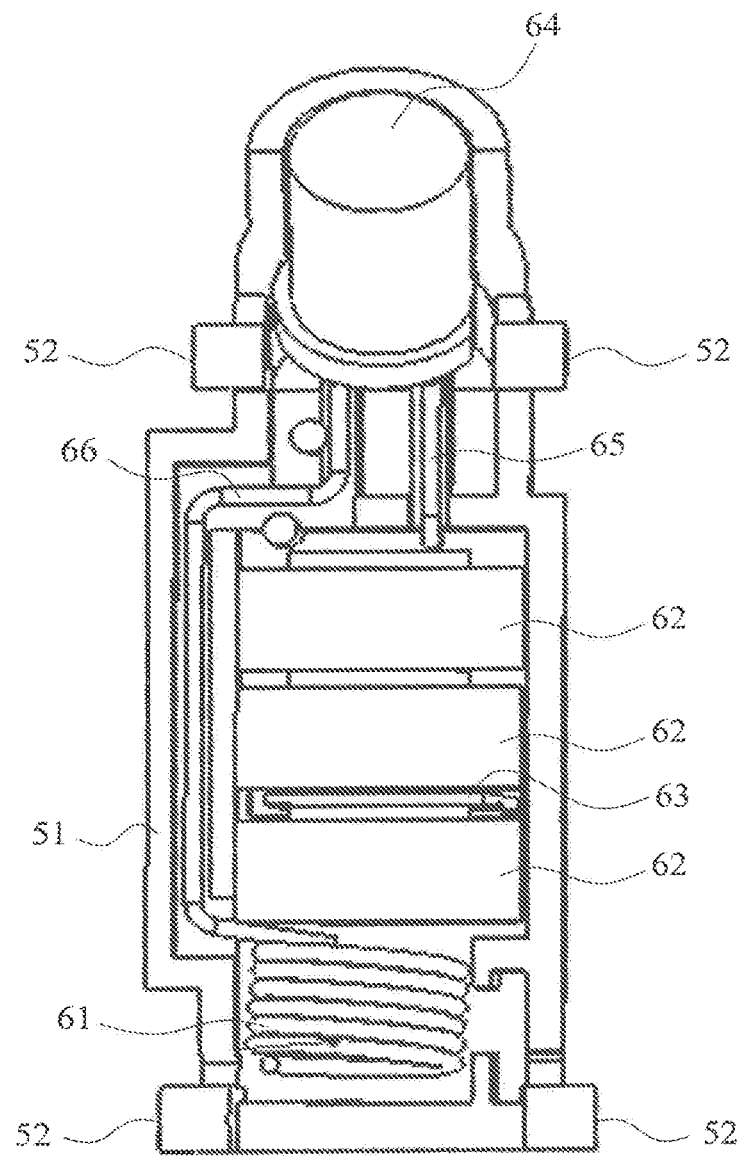
FIG. 6 is a front view of the illumination assembly of FIG. 5.

Please refer to FIGS. 5-6. FIG. 5 is a schematic view of the illumination assembly 50 of the illuminated surgical retractor 10 of FIG. 1. FIG. 6 is a front view of the illumination assembly 50 of FIG. 5. The light case 51 contains the light source 64, the batteries 62, a spring 61, and the pull tab 63. The light source 64 has electrical leads 65 and 66 which are cut to an appropriate length and bent such that the electrical lead 65 makes an electrical contact with the anode or cathode of one battery 62 and the electrical lead 66 makes an electrical contact with the spring 61. In this embodiment, the spring 61 is made of a metal such as stainless steel. In other embodiments, other electrically conductive materials suitable for producing a spring may be used. The spring 61 makes an electrical contact with the opposite battery polarity other than that previously mentioned, and the spring 61 makes this contact with one battery 62.

The spring 61 is assembled in a compressed condition such that the spring 62 applies a force to the batteries 62, the pull tab 63, and the light source leads 65 and 66. This force insures the electrical contact between the batteries 62, the light source leads 65 and 66, the spring 61, and the pull tab 63. The pull tab 63 is made of an electrically insulative material such as polymer, plastic or film. The pull tab 63 prevents an electric current from flowing to the light source 64 while the pull tab 63 is inserted between two of the batteries 62. The removal of the pull tab 63 will cause the spring 61 to push together the batteries 62 and allow an electric current to flow to the light source 64. Thus, light is emitted from the light source 64. The application of the pull tab 63 is a very low cost method to control the energizing of the electrical circuit. In other embodiments, a switch may be utilized instead of the pull tab 63 to complete the circuit of the batteries 62 and the light source 64. The person having ordinary skill in the art will easily understand these other embodiments.

As shown in FIGS. 5-6, the illumination assembly 50 includes a light case 51. Retaining tabs 52 protrude from the light case 51. The light case 51 is integrally molded and in this embodiment is made of a moldable material such as plastic or nylon although in other embodiments other materials may be used. Moreover, the illumination assembly 50 includes a plurality of retaining tabs 52. To be more specific, the retaining tabs 52 are located at the distal end of the legs 53, and are protruded at right angles to the legs 53. In the present embodiment, the retaining tabs 52 are initially compressed when inserted into an acceptance slots 71 (not shown in FIGS. 5-6).

Figure 7:
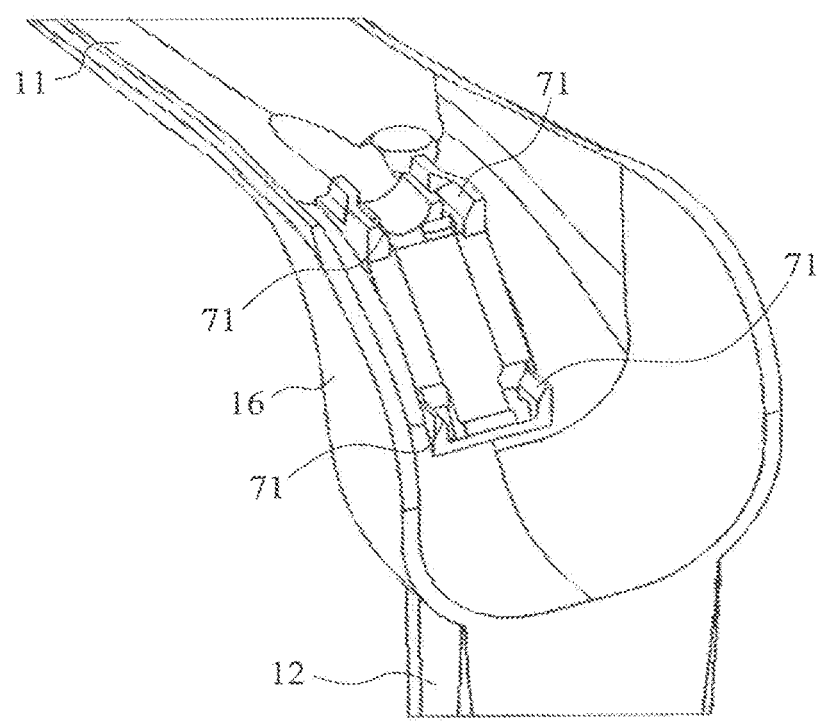
FIG. 7 is a partially enlarged view of the illuminated surgical retractor of FIG. 1 with the illumination assembly removed.
Figure 8:
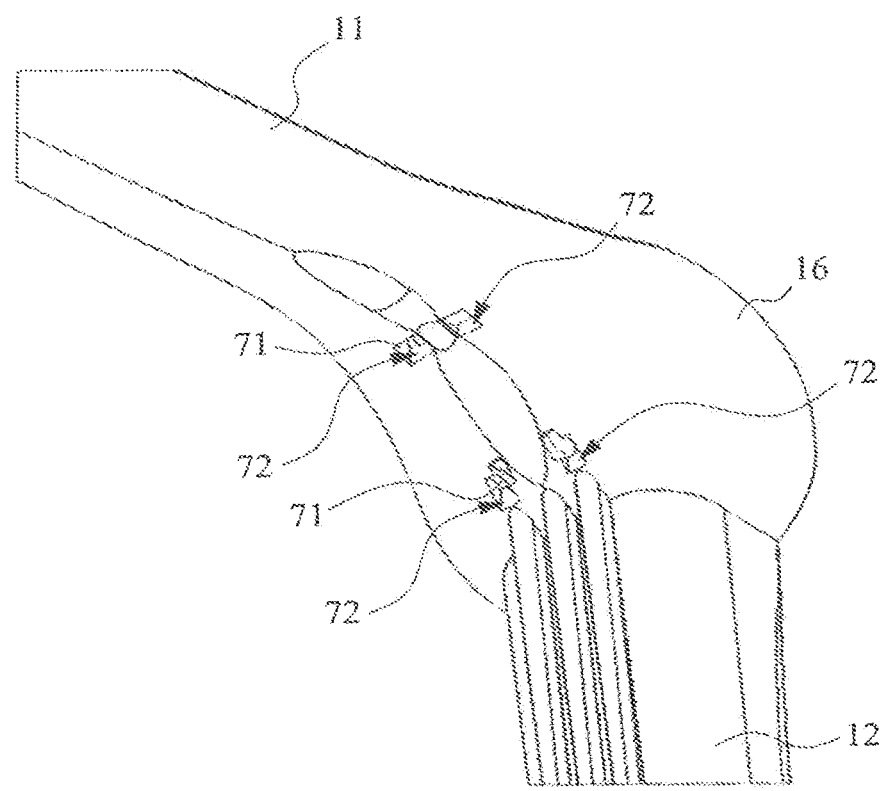
FIG. 8 is a partially enlarged view of the illuminated surgical retractor of FIG. 1 with the illumination assembly removed.

Please refer to FIGS. 7-8. FIGS. 7-8 are partially enlarged views of the illuminated surgical retractor 10 of FIG. 1 with the illumination assembly 50 removed. As shown in FIGS. 7-8, the illuminated surgical retractor 10 further includes a plurality of acceptance slots 71 and an acceptance cavity 72. The acceptance slots 71 are located vertically, horizontally or at an angle with the curved section 16, and are configured for accepting the retaining tabs 52. The acceptance slots 71 are in communication with the acceptance cavity 72 (shown in FIG. 8). When the retaining tabs 52 are inserted fully into the acceptance slots 71, the retaining tabs 52 arrive at the acceptance cavity 72. The acceptance cavity 72 is arranged to remove compression on the retaining tabs 52 and will inhibit the removal of the retaining tab 52 from the acceptance cavity 72. In the present embodiment, the acceptance cavity 72 is recessed into the retractor component 15 such that the retaining tabs 52 will not protrude from the surface of retractor component 15. The lack of any protrusion allows for a smooth surface of the blade 11 and the handle 12, and an angled area between the blade 11 and the handle 12 prevents tissue irrigation during medical procedures.

The present disclosure of the retaining tabs 52, the retaining legs 53, the acceptance slots 71, and the acceptance cavity 72 allows novel flexibility in the creation of injection molds for the retractor component 15. In the present embodiment. The injections slots are vertical, as required for molds that are designed to be released vertically. The person having ordinary skill in the art of injection molding will easily recognize that the shape of the reflector component 15 requires molds that release vertically. Other embodiments of the retractor component 15 may contain shapes that require horizontal mold releases and thus will have horizontal acceptance slots and cavities. The non-directional shape of the retaining tab 52 allows the illumination assembly 50 to be utilized with either vertically released molds or horizontally released molds. The use of a common illumination assembly 50 for a wide variety of retractor shapes dramatically lowers the cost of the illuminated surgical retractor 10.

This embodiment of the present disclosure clearly shows a novel, low cost illumination assembly 50 attached in a unique location of the illuminated surgical retractor 10 which eliminates the expensive electrical and/or optical interconnection between the handle 12 and the blade 11 of previous disclosures. The illumination assembly 50 is attached to the illuminated surgical retractor 10 in a novel way so as to be compatible with a wide assortment of retractor shapes which can be molded vertically or horizontally. The chemical capacity of the batteries 62 is sufficient for only a single use and the illuminated surgical retractor is discarded after the single use. The intrinsic low cost of the present disclosure makes the illuminated surgical retractor 10 economically attractive, and eliminates the inefficiency and expense of cleaning and re-sterilization. Recent evidence is emerging that procedures for cleaning and sterilization are often flawed in practice, resulting in possible cross contamination of patients. The present disclosure completely eliminates the risk of cross contamination by insuring that each of the illuminated surgical retractor 10 is only used once.

In summary, when compared with the prior art, the embodiments of the present disclosure mentioned above have at least the following advantages:

(1) The non-directional shape of the retaining lab allows the illumination assembly to be utilized with either vertically released molds or horizontally released molds. This use of a common illumination assembly for a wide variety of retractor shapes dramatically lowers the cost of the illuminated surgical retractor.

(2) The chemical capacity of the batteries is sufficient for only a single use and the illuminated surgical retractor is discarded after the single use. The intrinsic low cost of the present disclosure makes the illuminated surgical retractor economically attractive, and eliminates the inefficiency and expense of cleaning and re-sterilization.

Although the present disclosure has been described in considerable detail with reference to certain embodiments thereof, other embodiments are possible. Therefore, the spirit and scope of the appended claims should not be limited to the description of the embodiments contained herein.

It will be apparent to the person having ordinary skill in the art that various modifications and variations can be made to the structure of the present disclosure without departing from the scope or spirit of the present disclosure. In view of the foregoing, it is intended that the present disclosure cover modifications and variations of the present disclosure provided they fall within the scope of the following claims.

What is claimed is:

1. An illuminated surgical retractor comprising:
   a blade having first and second opposing surfaces;
   a handle extending in a first direction at an angle from a proximal end of the blade;
   an illumination assembly comprising at least one direct light source positioned to directly emit light toward a distal end of the blade, wherein:
   the first surface of the blade faces away from the first direction,
   the illumination assembly abuts the first surface of the blade, and
   the illumination assembly includes a cover abutting the first surface of the blade to partially enclose the at least one direct light source, wherein the direct light source is sandwiched between the cover and the first surface of the blade.

2. The illuminated surgical retractor in accordance with claim 1, wherein the illumination assembly does not abut the second surface of the blade.

3. The illuminated surgical retractor in accordance with claim 1, wherein the blade includes a curved portion and a main blade portion, said curved portion forming a joint between the handle and the main blade portion, and wherein the illumination assembly abuts the curved portion of the blade.

4. The illuminated surgical retractor of claim 1, wherein the illumination assembly further comprises at least one power source and a switch for energizing the direct light source, wherein the cover partially encloses the at least one power source and the switch.

5. The illuminated surgical retractor of claim 4, wherein the switch comprises one of a removable tab extending from an opening in the cover of the illumination assembly and an electrical switch.

6. The illuminated surgical retractor of claim 1, wherein the illumination assembly does not include a light pipe.

7. The illuminated surgical retractor of claim 1, wherein the illumination assembly is non-releasably integrated into the retractor.

8. The illuminated surgical retractor of claim 1, wherein the blade and the handle are molded from a high strength plastic.

9. The illuminated surgical retractor of claim 1, wherein a distal end of the blade is wider than the proximal end of the blade.

10. The illuminated surgical retractor of claim 1, wherein the blade includes a lip at the distal end for retaining tissue.

11. An illuminated surgical retractor comprising:
    a blade including a curved portion at a proximal end thereof and a main blade portion extending from the curved portion;
    a handle extending at an angle from the proximal end of the blade, said curved portion forming a joint between the handle and the main blade portion;
    an illumination assembly comprising at least one direct light source positioned to emit light toward a distal end of the blade,
    wherein the illumination assembly includes a cover partially enclosing the at least one direct light source, said cover extending along the curved section of the blade.

12. The illuminated surgical retractor of claim 11, wherein the direct light source is angled so that substantially all of the light emitted by the direct light source travels to the distal end of the blade.

13. The illuminated surgical retractor of claim 11, further comprising at least one power source and a switch for energizing the light source.

14. The illuminated surgical retractor of claim 11, wherein the curved portion includes a recess for accommodating the illumination assembly.

15. The illuminated surgical retractor of claim 11, wherein the illumination assembly is non-releasably integrated into the retractor.

16. The illuminated surgical retractor of claim 11, wherein the blade and the handle are formed from high strength plastic.

17. An illuminated surgical retractor comprising:
    a blade having first and second opposing surfaces;
    a handle extending in a first direction at an angle from a proximal end of the blade;
    an illumination assembly comprising at least one direct light source positioned to emit light toward the distal end of the blade, wherein:
    the first surface of the blade faces away from the first direction, and
    the illumination assembly includes a cover partially enclosing the at least one direct light source and extending along a portion of the first surface of the blade, wherein the direct light source is sandwiched between the cover and the first surface of the blade.

18. The illuminated surgical retractor of claim 17, wherein the direct light source is angled so that substantially all of the light emitted by the direct light source travels to the distal end of the blade.

19. The illuminated surgical retractor of claim 17, further comprising at least one power source and a switch for energizing the direct light source, wherein the cover partially encloses the at least one power source and the switch.

20. The illuminated surgical retractor of claim 17, wherein the illumination assembly is non-releasably integrated into the retractor.

21. The illuminated surgical retractor of claim 17, wherein the blade and the handle are formed from high strength plastic.

* * * * *